US006618139B2

(12) United States Patent
Erath

(10) Patent No.: US 6,618,139 B2
(45) Date of Patent: Sep. 9, 2003

(54) TORCH GLASSWARE FOR USE WITH INDUCTIVELY COUPLED PLASMA-OPTICAL EMISSION SPECTROMETER

(75) Inventor: Michael Erath, Uberlingen (DE)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

(21) Appl. No.: 09/757,893

(22) Filed: Jan. 10, 2001

(65) Prior Publication Data

US 2002/0089666 A1 Jul. 11, 2002

Related U.S. Application Data

(60) Provisional application No. 60/175,988, filed on Jan. 13, 2000.

(51) Int. Cl.[7] .................................................. G01J 3/30
(52) U.S. Cl. ..................................... 356/316; 219/121.5
(58) Field of Search ................................. 356/215, 316; 219/121.49, 121.5

(56) References Cited

U.S. PATENT DOCUMENTS

| | | | | |
|---|---|---|---|---|
| 4,517,495 A | * | 5/1985 | Piepmeier | 315/111.21 |
| 4,678,428 A | * | 7/1987 | Tanaka et al. | 431/76 |
| 4,766,287 A | * | 8/1988 | Morrisroe et al. | 219/121.52 |
| 5,186,621 A | * | 2/1993 | Pennington | 431/354 |
| 5,367,163 A | * | 11/1994 | Otsuka et al. | 250/288 |
| 5,642,190 A | * | 6/1997 | Krupa et al. | 356/316 |
| 6,122,050 A | | 9/2000 | Rutzke | |
| 6,166,379 A | | 12/2000 | Montaser et al. | |

FOREIGN PATENT DOCUMENTS

JP          05126740     *   5/1993    ................. 356/316

* cited by examiner

Primary Examiner—Mark Tremblay
(74) Attorney, Agent, or Firm—St. Onge Steward Johnston & Reens LLC

(57) ABSTRACT

Torch glassware for use with inductively coupled plasma-optical emission spectrometers is provided. The glassware includes an outer tube and a stream of cool inert gas flowing radially within the inner surface thereof such that the cool inert gas creates a cushion between the tube and hot plasma contained within the stream of cool inert gas. The outer tube includes a sidewall having an open end and having a slot passing therethrough. The slot extends longitudinally along the sidewall from the open end thereof and is defined at least in part by a first longitudinal edge and a second longitudinal edge. The first longitudinal edge is offset radially inwardly from the second longitudinal edge. Stated another way, the tube includes a fixed center, and a distance between the fixed center and the first longitudinal edge is smaller than a distance between the fixed center and the second longitudinal edge.

18 Claims, 2 Drawing Sheets

TORCH GLASSWARE FOR USE WITH INDUCTIVELY COUPLED PLASMA-OPTICAL EMISSION SPECTROMETER

This application claims the benefit of provisional application No. 60/175,988 filed Jan. 13, 2000.

FIELD OF THE INVENTION

The present invention relates to the field of spectrometers used for quantitative analysis, and more particularly to torch glassware for use with inductively coupled plasma-optical emission spectrometers.

BACKGROUND OF THE INVENTION

Spectrometric analysis entails the precise measurement of the interaction between a sample (analyte) and an energy source in order to determine the chemical composition of the aforementioned analyte. Techniques of spectrometric analysis vary both in the state in which an analyte is placed prior to testing, and in the type of energy to which the analyte is exposed. However, all spectrometric techniques are based upon relating the energy-dependent behavior of an analyte to its constituent quantity and quality.

In emission spectrometry the analyte to be tested is supplied with energy from a non-radiative external energy source, usually heat from a plasma flame or electric wire. Upon exposure to an external energy source, the analyte gains energy, and typically re-emits this energy in the form of photons. The quantity and scatter distribution of these released photons is then measured by a light sensitive spectrometer, and used for quantitation, since the energy emission pattern of an analyte is specific for each constituent of that analyte. Thus, this allows a quantitative analysis of the elemental composition of that analyte to be made.

The Inductively Coupled Plasma-Optical Emission Spectrometer (ICP-OES) is a species of plasma spectrometer that can quantitatively analyze various sample/analyte types to determine their elemental composition. Common sample sources include water, plant and animal tissues, geological specimens and industrial samples. Plasma spectrometers typically use a radio frequency and a stream of argon in a torch to generate plasma whose temperature can reach 10,000 degrees centigrade. The hot plasma created in this way is flame-like in appearance and is as hot as the surface of the sun. A stream of argon then carries an aerosol of the sample to be analyzed into the central channel of the plasma. As the sample encounters the hotter portion of the plasma its atoms go from their ground state to an excited state, or become ionizable, a situation in which some of the sample's electrons are stripped from outer valence shells. Eventually the electrons return to their ground states, and during this change in energy status they release a characteristic wavelength of light for each element present in the sample. It is this characteristic, or signature spectra pattern of light, which is used to identify given elements.

Referring now to FIG. 1, an outer tube 10 of a traditional ICP-OES torch is illustrated. Tube 10 is typically open-ended and may be formed of quartz. Proximate to its open end, tube 10 includes a substantially cylindrical outer surface 12 and a substantially cylindrical inner surface 14. The plasma created by the stream of argon in the torch is, as described above, extremely hot. It is therefore necessary to inhibit the hot plasma from contacting tube 10. If the plasma does contact tube 10, the tube may be destroyed, or the life of tube 10 may be greatly reduced. To this end, a stream of relatively cool inert gas (illustrated by arrows 16) is provided. The stream of cool inert gas is flowed generally radially within the inner surface 14, with the hot plasma being contained within the stream of cool inert gas. Thus, the hot plasma is inhibited from contacting tube 10 by this "cushion" of cool inert gas.

In a conventional radially-viewed ICP-OES, the emitted light is viewed from the side of a vertically oriented plasma and focused on the entrance slit of the spectrometer. Referring now to FIG. 2, such had traditionally required that the emitted light be viewed through the sidewall of the outer tube 20 of the torch. However, it was discovered that more accurate results could be obtained by providing a slot 22 passing through the sidewall of the tube 20. The slot 22 typically extends from the open end of the tube 20 longitudinally up the side wall thereof far enough that the entrance slit of the spectrometer is not obscured by the sidewall.

While this design provides more accurate results, it introduces new problems of its own. Tube 20 is still defined by a substantially cylindrical outer surface 24 and a substantially cylindrical inner surface 26, and a stream of relatively cool inert gas (illustrated by arrows 28) flowing generally radially within the inner surface 26 is still provided in order to inhibit the hot plasma from contacting tube 20. However, it has been discovered that the lifespan of the tube 20 is greatly reduced as compared to tube 10 which included no slot. In particular, it has been discovered that when a tube 20 which includes a slot 22 is used, devitrification occurs adjacent the slot 22, particularly along the side of the slot 22 downstream with respect to the radially flowing cool inert gas. It has been discovered that this problem is caused by the interruption in the flow of cool inert gas caused by the slot. More specifically, as the gas flows past slot 22, at least a portion of the gas escapes through slot 22 (illustrated by arrows 30). This escaping gas causes the "cushion" of cool inert gas proximate the slot 22 to degrade, and a portion of the hot plasma may be allowed to contact the inner surface 26 of tube 20 (as illustrated by arrow 32). In more extreme cases, the hot plasma may be able to contact the edge 34 of the slot 22 downstream with respect to the radially flowing cool inert gas (indicated by arrow 38), or even to escape tube 20 through slot 22 altogether and contact the outer surface 24 of tube 20. This contact between the hot plasma and the tube 20 may cause the lifespan of the tube to be seriously shortened.

What is desired, therefore, is torch glassware for use with inductively coupled plasma-optical emission spectrometers which includes an outer tube and a stream of cool inert gas flowing radially within the inner surface thereof such that the cool inert gas creates a cushion between the tube and hot plasma contained within the stream of cool inert gas, which includes a slot passing through the sidewall of the tube to provide optimum results, which is designed such that the cushion of cool inert gas is not degraded by the slot, and which has a lifespan similar to the lifespan of torch glassware without a slot.

SUMMARY OF THE INVENTION

Accordingly, it is an object of the present invention to provide torch glassware for use with inductively coupled plasma-optical emission spectrometers which includes an outer tube and a stream of cool inert gas flowing radially within the inner surface thereof such that the cool inert gas creates a cushion between the tube and hot plasma contained within the stream of cool inert gas.

Another object of the present invention is to provide torch glassware having the above characteristics and which includes a slot passing through the sidewall of the tube to provide optimum results.

A further object of the present invention is to provide torch glassware having the above characteristics and which is designed such that the cushion of cool inert gas is not degraded by the slot.

Still another object of the present invention is to provide torch glassware having the above characteristics and which has a lifespan similar to the lifespan of torch glassware without a slot.

These and other objects of the present invention are achieved by provision of torch glassware for use with inductively coupled plasma-optical emission spectrometers having an outer tube and a stream of cool inert gas flowing radially within the inner surface thereof such that the cool inert gas creates a cushion between the tube and hot plasma contained within the stream of cool inert gas. The outer tube includes a sidewall having an open end and having a slot passing therethrough. The slot extends longitudinally along the sidewall from the open end thereof and is defined at least in part by a first longitudinal edge and a second longitudinal edge. The first longitudinal edge is offset radially inwardly from the second longitudinal edge. Stated another way, the tube includes a fixed center, and a distance between the fixed center and the first longitudinal edge is smaller than a distance between the fixed center and the second longitudinal edge. Preferably, the first longitudinal edge is upstream of the second longitudinal edge with respect to the cool inert gas flowing radially within the inner surface of the tube.

In one preferred embodiment, such an arrangement is achieved by providing a portion of the sidewall with a substantially cylindrical in shape, and by deflecting a portion of the sidewall adjacent to the first edge inwardly. Preferably, the slot is further defined at least in part by an axial edge, and a portion of the sidewall adjacent to the axial edge is also deflected inwardly. Most preferably, the axial edge is curved.

The invention and its particular features and advantages will become more apparent from the following detailed description considered with reference to the accompanying drawings.

DETAILED DESCRIPTION OF THE INVENTION

Figure 3:
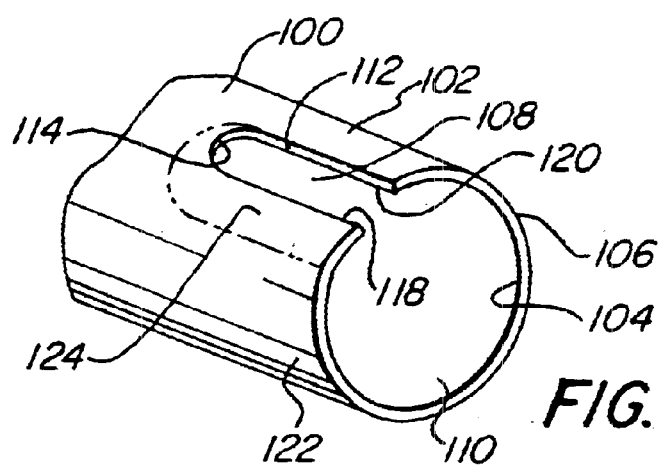
FIG. 3 is a side isometric view of the outer tube of torch glassware for use with inductively coupled plasma-optical emission spectrometers in accordance with the present invention; and, FIG. 4 is an end view of the outer tube of the torch glassware of FIG. 3.
Figure 4:
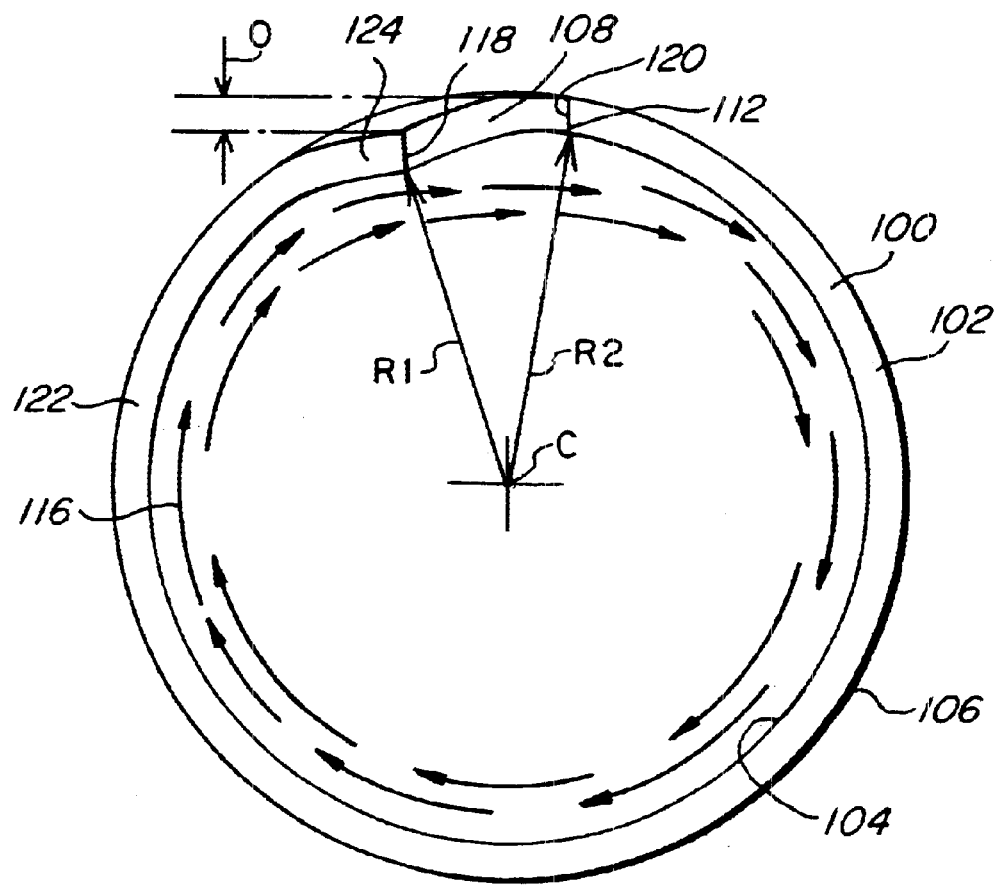

Referring to FIGS. 3 and 4, an outer tube 100 of torch glassware for use with inductively coupled plasma-optical emission spectrometers (ICP-OES) in accordance with the present invention is shown. Tube 100 is defined by a sidewall 102 having an inner surface 104 and an outer surface 106. As discussed above, and is known in the art, the sidewall 102 of tube 100 has a slot 108 passing therethrough and extending from the open end 110 of the tube 100 longitudinally up the side wall 102 thereof far enough that the entrance slit of the spectrometer (not shown) is not obscured by the sidewall 102. The slot is defined on two sides by longitudinal edges 112 and on a third side opposite the open end 110 of the tube 100 by an axial edge 114. The axial edge 114 may be curved (as shown in FIG. 3), straight, or any of numerous other configurations, as are known in the art.

Also as is known in the art, a stream of relatively cool inert gas (illustrated by arrows 116) is provided. The stream of cool inert gas is flowed generally radially within the inner surface 104 of tube 100, with hot plasma being contained within the stream of cool inert gas. Thus, the hot plasma is inhibited from contacting tube 100 by this "cushion" of cool inert gas. As this process is well-known in the art of ICP-OES, it is not fully described herein.

Slot 108 should be wide enough such that the entrance slit of the spectrometer (not shown) is not obscured by the sidewall 102. However, it should be understood that the width of slot 108 should be as small as is practicable such as to minimize any disturbances of the cool inert gas flowing generally radially within the inner surface 104 of tube 100.

Figure 1:
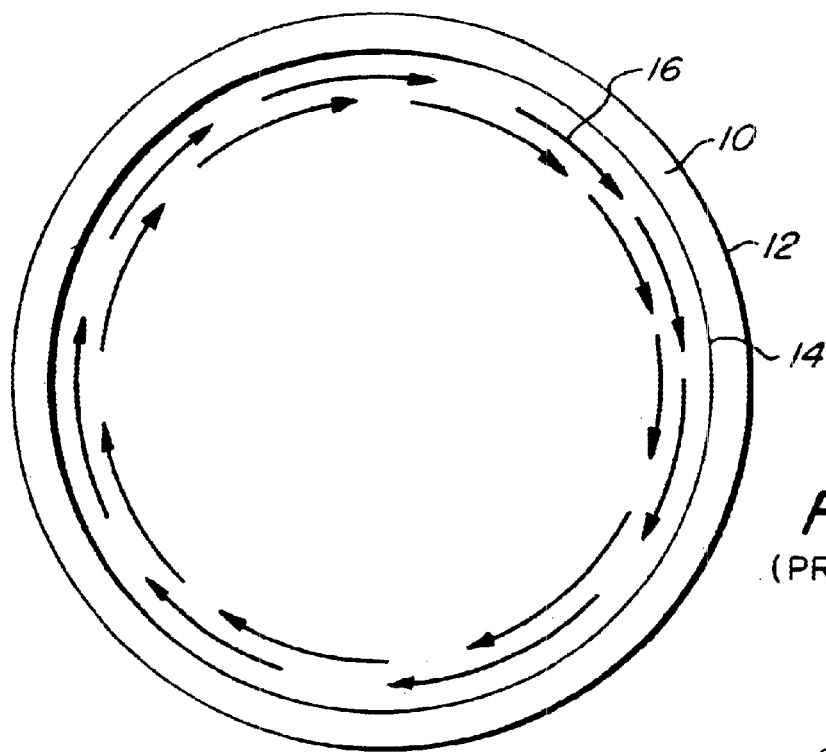
FIG. 1 is an end view of the outer tube of prior art torch glassware for use with inductively coupled plasma-optical emission spectrometers.
Figure 2:
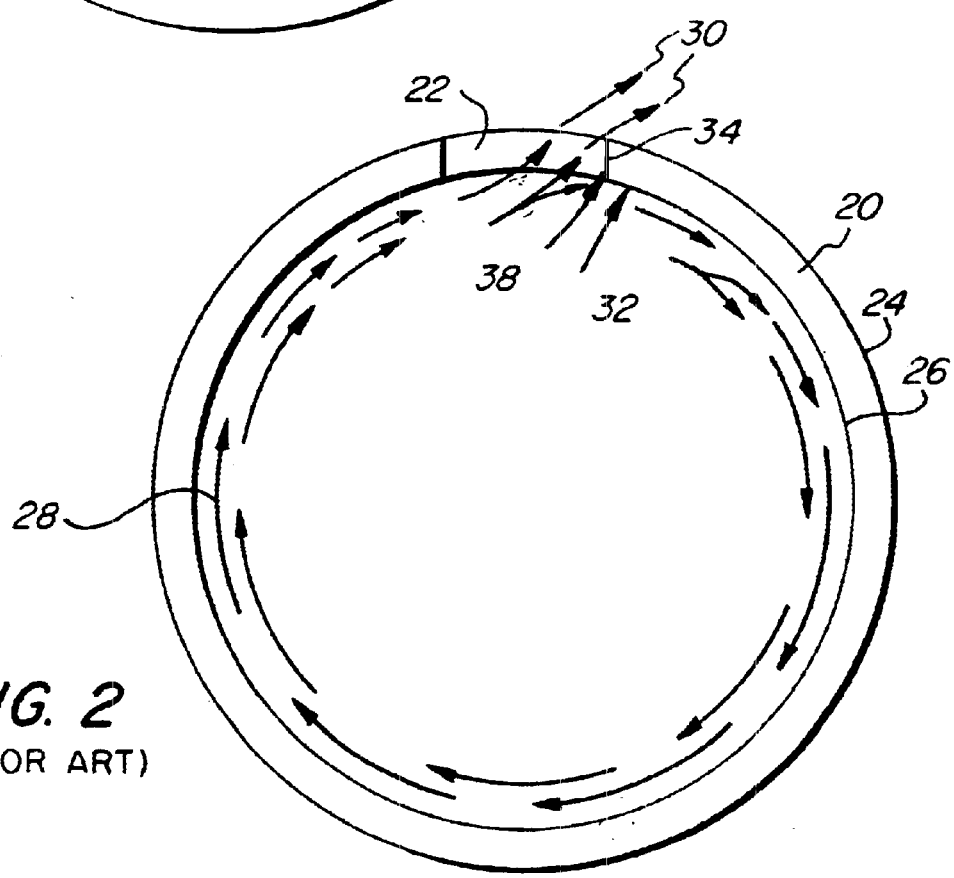
FIG. 2 is an end view of the outer tube of other prior art torch glassware for use with inductively coupled plasma-optical emission spectrometers which includes a slot therein to provide optimum results.

As discussed above with respect to FIG. 2, which illustrates a prior art tube 20, when tube 20 is defined by a substantially cylindrical outer surface 24 and a substantially cylindrical inner surface 26, and a stream of relatively cool inert gas (illustrated by arrows 28) flowing generally radially within the inner surface 26 is still provided in order to inhibit the hot plasma from contacting tube 20, it has been discovered that degradation of the tube 20 may be caused by the interruption in the flow of cool inert gas caused by the slot 22. More specifically, as the gas flows past slot 22, at least a portion of the gas escapes through slot 22 (illustrated by arrows 30). This escaping gas causes the "cushion" of cool inert gas proximate the slot 22 to degrade, and a portion of the hot plasma may be allowed to contact the inner surface 26 of tube 20 (as illustrated by arrow 32).

It has been found that this problem may be remedied, however, if the interruption of the flow of the cool inert gas, and the amount of gas allowed to escape from the tube, are minimized. To this end, the sidewall 102 of tube 100 is shaped such that the upstream edge 118 of slot 108 (i.e., the edge 112 of the slot over which the gas first passes) is offset toward the center of the tube 100 as compared with the downstream edge 120 of slot 108 (i.e., the edge 112 of the slot over which the gas passes second). Stated another way, the distance R1 from a fixed center point C of tube 100 to the upstream edge 118 of slot 108 is smaller than the distance R2 from the fixed center point C to the downstream edge 120 of slot 108. The distance of the offset O may vary, and will be defined by, among other considerations, the width of the slot 108, the width of the sidewall 102 of tube 100, and the velocity of flow of the cool inert gas. Preferably, however, the offset 0 is of such magnitude that substantially none of the cool inert gas is allowed to escape through slot 108.

The offset of the upstream edge 118 of slot 108 as compared with the downstream edge 120 of slot 108 may be achieved in any of numerous ways. For example, in one unillustrated embodiment, tube 100 may be created such that a cross section of the sidewall 102 of tube 100 proximate the open end 110 thereof lies on a spiral. In other words, the sidewall 102 winds around the fixed center point C at a continuously decreasing distance from the downstream edge 120 of slot 108 to the upstream edge 118 of slot 108.

In the preferred embodiment shown in FIGS. 3 and 4, however, a major portion 122 of the sidewall 102 of tube 100 is substantially cylindrical in shape, with only a portion 124 (shown as dashed lines in FIG. 3) adjacent to the upstream edge 118 of slot 108 deflecting inwardly such that the distance R1 from a fixed center point C of tube 100 to the upstream edge 118 of slot 108 is smaller than the distance R2 from the fixed center point C to the downstream edge 120 of slot 108. It should be understood that the deflection of portion 124 should be smooth and that portion 124 may extend around and encompass at least a portion of axial edge 114 of slot 108 such that substantially none of the cool inert gas is allowed to escape through slot 108, and such that any disturbances of the cool inert gas flowing generally radially within the inner surface 104 of tube 100 are minimal.

The present invention, therefore, provides torch glassware for use with inductively coupled plasma-optical emission spectrometers which includes an outer tube and a stream of cool inert gas flowing radially within the inner surface thereof such that the cool inert gas creates a cushion between the tube and hot plasma contained within the stream of cool inert gas, which includes a slot passing through the sidewall of the tube to provide optimum results, which is designed such that the cushion of cool inert gas is not degraded by the slot, and which has a lifespan similar to the lifespan of torch glassware without a slot.

Although the invention has been described with reference to a particular arrangement of parts, features and the like, these are not intended to exhaust all possible arrangements or features, and indeed many other modifications and variations will be ascertainable to those of skill in the art.

What is claimed is:

1. Torch glassware for use with inductively coupled plasma-optical emission spectrometers having an outer tube and a stream of cool inert gas flowing radially within the inner surface thereof such that the cool inert gas creates a cushion between the tube and hot plasma contained within the stream of cool inert gas, said outer tube comprising:

a sidewall, said sidewall having an open end and having a slot passing therethrough, the slot extending longitudinally along said sidewall from the open end thereof and being defined at least in part by a first longitudinal edge and a second longitudinal edge; and wherein said first longitudinal edge is offset radially inwardly from the second longitudinal edge.

2. The torch glassware of claim 1 wherein the first longitudinal edge is upstream of the second longitudinal edge with respect to the cool inert gas flowing radially within the inner surface of the tube.

3. The torch glassware of claim 1 wherein the tube includes a fixed center, and wherein a distance between the fixed center and the first longitudinal edge is smaller than a distance between the fixed center and the second longitudinal edge.

4. The torch glassware of claim 1 wherein a portion of said sidewall is substantially cylindrical in shape, and wherein a portion of said sidewall adjacent to the first edge is deflected inwardly.

5. The torch glassware of claim 4 wherein the slot is further defined at least in part by an axial edge, and wherein a portion of said sidewall adjacent to the axial edge is deflected inwardly.

6. The torch glassware of claim 5 wherein the axial edge is curved.

7. Torch glassware for use with inductively coupled plasma-optical emission spectrometers having an outer tube and a stream of cool inert gas flowing radially within the inner surface thereof such that the cool inert gas creates a cushion between the tube and hot plasma contained within the stream of cool inert gas, said outer tube comprising:

a sidewall, said sidewall having an open end and having a slot passing therethrough, the slot extending longitudinally along said sidewall from the open end thereof and being defined at least in part by a first longitudinal edge and a second longitudinal edge;

wherein the tube includes a fixed center; and wherein a distance between the fixed center and the first longitudinal edge is smaller than a distance between the fixed center and the second longitudinal edge.

8. The torch glassware of claim 7 wherein the first longitudinal edge is upstream of the second longitudinal edge with respect to the cool inert gas flowing radially within the inner surface of the tube.

9. The torch glassware of claim 7 wherein said first longitudinal edge is offset radially inwardly from the second longitudinal edge.

10. The torch glassware of claim 7 wherein a portion of said sidewall is substantially cylindrical in shape, and wherein a portion of said sidewall adjacent to the first edge is deflected inwardly.

11. The torch glassware of claim 10 wherein the slot is further defined at least in part by an axial edge, and wherein a portion of said sidewall adjacent to the axial edge is deflected inwardly.

12. The torch glassware of claim 11 wherein the axial edge is curved.

13. Torch glassware for use with inductively coupled plasma-optical emission spectrometers having an outer tube and a stream of cool inert gas flowing radially within the inner surface thereof such that the cool inert gas creates a cushion between the tube and hot plasma contained within the stream of cool inert gas, said outer tube comprising:

a sidewall, said sidewall having an open end and having a slot passing therethrough, the slot extending longitudinally along said sidewall from the open end thereof and being defined at least in part by a first longitudinal edge and a second longitudinal edge; and wherein a portion of said sidewall is substantially cylindrical in shape, and wherein a portion of said sidewall adjacent to the first edge is deflected inwardly.

14. The torch glassware of claim 13 wherein the first longitudinal edge is upstream of the second longitudinal edge with respect to the cool inert gas flowing radially within the inner surface of the tube.

15. The torch glassware of claim 13 wherein the tube includes a fixed center, and wherein a distance between the fixed center and the first longitudinal edge is smaller than a distance between the fixed center and the second longitudinal edge.

16. The torch glassware of claim 13 wherein said first longitudinal edge is offset radially inwardly from the second longitudinal edge.

17. The torch glassware of claim 13 wherein the slot is further defined at least in part by an axial edge, and wherein a portion of said sidewall adjacent to the axial edge is deflected inwardly.

18. The torch glassware of claim 17 wherein the axial edge is curved.

* * * * *